(12) United States Patent
Mittermeyer (10) Patent No.: US 9,152,766 B2
(45) Date of Patent: Oct. 6, 2015

(54) COMPUTER-ASSISTED INFUSION PLANNING AND SIMULATION

(75) Inventor: Stephan Mittermeyer, Munich (DE)

(73) Assignee: Brainlab AG, Feldkirchen (DE)

( * ) Notice: Subject to any disclaimer, the term of this patent is extended or adjusted under 35 U.S.C. 154(b) by 125 days.

(21) Appl. No.: 14/000,731

(22) PCT Filed: Mar. 3, 2011

(86) PCT No.: PCT/EP2011/053156
§ 371 (c)(1),
(2), (4) Date: Aug. 21, 2013

(87) PCT Pub. No.: WO2012/116747
PCT Pub. Date: Sep. 7, 2012

(65) Prior Publication Data
US 2013/0322714 A1    Dec. 5, 2013

(51) Int. Cl.
*G06K 9/00* (2006.01)
*G06F 19/00* (2011.01)
*A61B 19/00* (2006.01)
*A61M 5/14* (2006.01)
*A61M 5/142* (2006.01)

(52) U.S. Cl.
CPC ............ *G06F 19/3437* (2013.01); *A61B 19/50* (2013.01); *G06F 19/3468* (2013.01); *A61B 2019/501* (2013.01); *A61M 2005/1406* (2013.01); *A61M 2005/14208* (2013.01); *A61M 2005/14292* (2013.01)

(58) Field of Classification Search
CPC ............ A61B 19/50; A61B 2019/501; A61M 2005/1406; G06F 19/3437; G06F 19/00
USPC ............................................... 382/128
See application file for complete search history.

(56) References Cited

U.S. PATENT DOCUMENTS

| | | | | |
|---|---|---|---|---|
| 5,771,895 | A * | 6/1998 | Slager ........................ | 600/462 |
| 6,064,904 | A * | 5/2000 | Yanof et al. ................. | 600/414 |
| 6,746,465 | B2 * | 6/2004 | Diederich et al. ........... | 606/192 |
| 8,105,307 | B2 | 1/2012 | Ponce | |
| 2003/0114751 | A1 | 6/2003 | Pedain et al. | |
| 2005/0020945 | A1* | 1/2005 | Tosaya et al. .................. | 601/2 |

(Continued)

FOREIGN PATENT DOCUMENTS

| | | |
|---|---|---|
| EP | 1 316 324 | 6/2003 |
| EP | 1 788 498 | 5/2007 |

(Continued)

OTHER PUBLICATIONS

International Search Report for International Application No. PCT/EP2011/053156 dated Dec. 2, 2011.

*Primary Examiner* — Gregory M Desire
(74) *Attorney, Agent, or Firm* — Tucker Ellis LLP (57) ABSTRACT

A method for planning an infusion of a medical liquid by an infusion apparatus comprising an infusion device, wherein the method comprises the steps of: acquiring planning scan data which represent a medical image of at least a body region (3) of a patient and are obtained by a planning scan before the infusion device is positioned; determining a planned device position from the planning scan data; acquiring verification scan data which represent a medical image of the region of the patient after the infusion device has been positioned; determining a source volume of the liquid from the verification scan data; and determining infusion parameters from the verification scan data and the source volume.

14 Claims, 4 Drawing Sheets

(56) References Cited

U.S. PATENT DOCUMENTS

| | | |
|---|---|---|
| 2007/0244387 A1* | 10/2007 | Rodriguez Ponce et al. .. 600/411 |
| 2008/0171934 A1* | 7/2008 | Greenan et al. ............... 600/411 |
| 2008/0228167 A1 | 9/2008 | Mittermeyer et al. |
| 2008/0312490 A1* | 12/2008 | Cropper et al. .................... 600/3 |
| 2009/0005668 A1* | 1/2009 | West et al. ..................... 600/407 |
| 2009/0171244 A1* | 7/2009 | Ning et al. ..................... 600/567 |
| 2010/0228534 A1* | 9/2010 | Gilboa et al. ...................... 703/11 |
| 2011/0092802 A1* | 4/2011 | Steckner ....................... 600/413 |
| 2011/0178359 A1* | 7/2011 | Hirschman et al. ................ 600/4 |
| 2012/0065494 A1* | 3/2012 | Gertner et al. ................ 600/411 |
| 2012/0302863 A1* | 11/2012 | O'Neill .......................... 600/407 |
| 2013/0322714 A1* | 12/2013 | Mittermeyer ................. 382/128 |
| 2015/0018596 A1* | 1/2015 | Schulz et al. ..................... 600/1 |

FOREIGN PATENT DOCUMENTS

| | | |
|---|---|---|
| EP | 1 788 499 | 5/2007 |
| EP | 1 905 466 | 4/2008 |
| EP | 1 970 001 | 9/2008 |
| WO | 01/85230 | 11/2001 |

* cited by examiner

COMPUTER-ASSISTED INFUSION PLANNING AND SIMULATION

This application is a national phase of International Application No. PCT/EP2011/053156 filed Mar. 3, 2011 and published in the English language.

The present invention relates to a method for planning an infusion of a medical liquid, a computer program which implements the method and a computer for miming the program.

Treatments comprising the infusion of a medical liquid are widely used and known. The medical liquid, or any therapeutic agent, is intended to infiltrate a target region or target tissue which is typically surrounded by non-target tissue. The term "infusion" means any administration of a liquid which has a medical effect on a body. The liquid can contain for example medicines, toxins, cells, genes, enzymes, proteins, antibodies, hormones, viruses or the like. The medical liquid is administered over a time period which can be anything between a few seconds and several days, weeks, months or even a patients remaining life. The infusion is performed by an infusion apparatus comprising an infusion device, such as a catheter, a cannula or a needle. The infusion device has one or more ports through which the medical liquid is discharged.

The delivery of the medical liquid by the infusion apparatus is controlled by infusion parameters. The infusion parameters can include at least one of: the duration of the infusion; the flow rate of the medical liquid; the viscosity of the medical liquid; and the amount of medically active substance in the liquid. Another important aspect is the position of the infusion, in particular the position of the port(s) of the infusion device and/or the trajectory of the infusion device. It is therefore advantageous to plan the infusion, which in particular includes determining the infusion parameters and/or the position of the infusion device.

The problem to be solved by the present invention is to improve the planning of an infusion, for example with regard to the amount of medical liquid introduced into the target region and/or the amount of medical liquid introduced into a non-target region.

This problem is solved by the method, program and computer according to the independent claims. Advantageous embodiments are described in the dependent claims.

The present invention relates to a method for planning an infusion of a medical liquid, the infusion being carried out using an infusion apparatus comprising an infusion device. In a typical environment, the infusion apparatus comprises a container for the medical liquid and means for enabling the infusion, such as a pump, piston or valve. The infusion device is the part of the infusion apparatus which is constituted to at least partly penetrate the body of a patient. The infusion device can, among other things, be a catheter, a cannula or a needle. The infusion device is to be positioned such that at least one outlet, or port, of the infusion device is located in or next to the target tissue. However, the actual positioning of the infusion device is not part of the present invention. The present invention relates only to planning the infusion using a computer, i.e. determining the infusion parameters and/or the infusion device position.

One step of the method involves acquiring planning scan data which represent a medical image of at least a body region of a patient. The planning scan data can be and preferably are obtained by a planning scan before the infusion device is positioned. The body region is a region comprising at least some and preferably all of the target tissue into which the medical liquid is to be infused.

The expression "acquiring data" in particular encompasses (within the framework of a data processing method) the scenario in which the data are determined by the data processing method or program. The meaning of "acquiring data" also in particular encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.), or via the interface (for instance, from another computer or a network). The data can achieve a state of being "ready for use" if an additional step is performed before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" may also involve commanding a device to obtain and/or provide the data to be acquired. The acquiring step in particular does not involve any invasive step which would represent a substantial physical interference with the body and require professional medical expertise to be carried out and entail a substantial health risk even when carried out with the required professional care and expertise. The acquiring step in particular does not involve a surgical step and in particular does not involve a step of treating a human or animal body using surgery or therapy. This also applies in particular to any steps directed to determining data. In order to distinguish the different data used by the present method, the data are designated (i.e. referred to) as "XY data" or the like and are defined by the information which they describe.

In this document, data which represent a medical image can be two-dimensional or three-dimensional data, i.e. data which represent a medical image in two or three spatial dimensions. The data can also represent several medical images over time, thus introducing an additional temporal dimension to the data. The medical image can be obtained by any suitable modality, such as for example magnetic resonance or nuclear spin resonance methods (MRI), computed tomography (CT) methods, X-ray methods or ultrasound methods.

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), X-ray tomography, magnetic resonance tomography (MRT or MRI), conventional X-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body.

The planning scan data can be further processed. Optionally, additional data such as diffusion tensor imaging (DTI) data and/or segmentation data can be derived from the planning scan data. These data are determined on the basis of the planning scan. DTI data represent information about how molecules, such as those of the medical liquid, will propagate. Propagation can for example occur through convection and/or diffusion. The DTI data might represent one distinct direction in which a molecule will propagate or preferably a probability distribution over a plurality of propagation directions. Segmentation data can be derived by segmenting the planning scan data, in order for example to identify the contour of a tumour in the medical image.

Another step of the method involves determining a planned device position from the planning scan data. In this step, a suitable and preferably optimum position of the infusion device is determined. The term "position" comprises at least the spatial position of the infusion device port(s) and preferably also the trajectory, i.e. the path, of at least a part of the infusion device within the body. The planned device position is preferably provided to a surgeon or a medical robot, who or which actually positions the infusion device.

The next step of the method involves acquiring verification scan data which represent a medical image of the region of the patient after the infusion device has been positioned. In the method step involving the verification scan data, the actual position of the infusion device can be detected and optionally compared to the planned device position. In addition, hemorrhages caused by positioning the infusion device can be detected. It should again be clarified that the actual positioning procedure is not part of the present invention. The step of acquiring the planning scan data is completed before the infusion device is positioned, and the step of acquiring the verification scan data does not begin before the positioning procedure is completed. The infusion device is therefore positioned at an intermediate stage between two steps of the present invention.

The next step of the method involves determining a source volume of the liquid from the verification scan data. This source volume is the volume from which the medical liquid propagates into the tissue. Typically, the source volume depends on at least one of: the type of infusion device; air bubbles in the body region; and the flow rate of the liquid. The type of infusion device and the flow rate of the liquid are known to influence the backflow length. Air bubbles constitute cavities in which the liquid accumulates before it propagates into the tissue. The term "source volume" encompasses a position and/or geometry, i.e. size and/or shape, of the volume.

The source volume consists of at least one of several possible parts. One such part is an injection volume in the vicinity of the infusion device port(s) which might be generated when the infusion device is positioned, for example by a stylet or a guidewire, or at the beginning of the infusion when air in the infusion device lumen is pushed into the tissue by the medical liquid. Another possible part of the source volume is the backflow volume which extends along the path of the infusion device, starting at the infusion device port. The backflow volume is generated when the medical liquid flows through the injection device and between the infusion device and the surrounding tissue, before it propagates into the tissue. The distance over which the liquid flows along the infusion device is called the backflow length.

The next step of the method involves determining the infusion parameters from the verification scan data and the source volume. In this step, the structure of the tissue and the source volume from which the medical liquid propagates into the tissue are used to determine the infusion parameters suitable for achieving a desired distribution of the medical liquid within the tissue. The infusion parameters can then be provided to the infusion apparatus.

The method optionally also comprises the step of performing image fusion of the planning scan data onto the verification scan data in order to obtain a transformation rule for data determined on the basis of the planning scan. The transformation rule is qualified to transform the planning scan data into the verification scan data. The additional data such as the DTI data and/or segmentation data have for example been determined on the basis of the planning scan, but are to be utilised in combination with the verification scan data, in particular in order to determine the infusion parameters. These additional data therefore have to be adapted to the scenario represented by the verification scan data. This is achieved by transforming the additional data using the transformation rule obtained. The transformation rule which transforms the planning scan data onto the scenario represented by the verification scan data is also appropriate for transforming additional data which are closely related to the planning scan data onto the scenario represented by the verification scan data.

Image fusion transformations are in particular designed to enable a seamless transition from one image to another. The transformation is in particular designed such that one of the first and second images is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed)

image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The planned position of the infusion device is preferably determined by simulating a distribution of the liquid for several virtual positions of the infusion device on the basis of the planning scan data and (automatically) selecting, as the planned position, the virtual position which best meets the conditions for a liquid distribution described by condition data. The condition data represent for example a desired or target liquid distribution.

Using this approach, several virtual positions are tested, and an appropriate position is chosen. The virtual position selected as the planned position can for instance be the first virtual position to fulfil the condition(s) represented by the condition data or the virtual position which results in the best liquid distribution. The definition of the best distribution can vary depending on the application and is represented by criteria data. The best distribution can be a distribution which exhibits at least a required concentration of the medical liquid in the target tissue and optionally a concentration in the non-target tissue which is as small as possible or below a certain threshold. The best distribution can also be a distribution which exhibits at least a required concentration in the target tissue and is obtained in the shortest infusion duration. The best distribution can of course also be defined in any other suitable way by appropriately defining the criteria data.

Furthermore, the liquid distribution for each virtual position of the infusion device is preferably simulated for a plurality of test sets of infusion parameters, i.e. for each virtual position, a plurality of test sets of infusion parameters is used as a condition for simulating the liquid distribution. A test set of infusion parameters can also be referred to as a candidate set. Optionally, the best test set of infusion parameters and the corresponding liquid distribution is determined for each virtual position, and the best virtual position is then determined.

In a preferred embodiment, the simulation is an iterative stochastic simulation. In each step, the propagation of the liquid is stochastically determined and applied to an initial distribution of the liquid. The modified distribution of the liquid is then used as the initial distribution in the next iteration step of the simulation.

The simulation preferably incorporates the structure of the body, in particular the structure of the tissue, in the region to be treated by the infusion. Information about the tissue density and/or the hydraulic conductivity and/or the blood flow through the tissue is in particular taken into account. This information can be determined from the additional data. It is also advantageous to incorporate properties of the medical liquid, such as its physical, chemical and/or biological properties. These can include any one or more of: the molecular or particle size of the liquid; the rate of diffusion of the liquid in the tissue; the electric charge of the molecule, the stability and half life; the metabolism of the patient, i.e. the interaction between the liquid and the tissue due to metabolic processes; a diffusion coefficient of the liquid; the pressure of the liquid; and the flow rate of the liquid.

The simulation can also incorporate infusion device parameters such as the inner diameter, surface finish or rigidity of the infusion device. The simulation of the liquid distribution preferably takes into account the position of the infusion device. Even though the infusion device is not included in the medical image represented by the planning scan data, the virtual position for which the distribution of the liquid is simulated is taken into account in the simulation. In particular, the liquid cannot propagate into the infusion device.

The infusion parameters are preferably determined by simulating a distribution of the liquid for several test sets of infusion parameters on the basis of the verification scan data and by (automatically) selecting, as the infusion parameters, the test set of infusion parameters which meet the conditions for a liquid distribution described by the condition data. The simulation is preferably performed in an analogous way to the simulation used to determine the planned position of the infusion device. The condition data are also preferably the same as those used to determine the planned position of the infusion device, but the simulation is based on the verification scan data instead of the planning scan data and also incorporates the previously determined source volume of the liquid. The additional data, such as the DTI data and/or the segmentation data, determined from the planning scan can be used in the simulation for determining the infusion parameters, in particular if these data are transformed using the transformation rule obtained as explained above.

In one embodiment, the first simulation for determining the infusion parameters is based on the test set of infusion parameters corresponding to the virtual position which was selected as the planned position of the infusion device. This is the test set which results in the best liquid distribution for said particular virtual position. This test set of infusion parameters is then considered to be at least similar to suitable infusion parameters.

Preferably, the method also optionally comprises the steps of acquiring monitoring scan data which represent a medical image of the region of the patient during the infusion by performing a monitoring scan, and determining actual liquid distribution data, which represent the actual distribution of the liquid in the body region, from the monitoring scan data. A contrast agent which is co-infused with the medical liquid can for example be detected. The progress of the infusion can be judged from the actual liquid distribution data, for example by comparing the actual liquid distribution data with expected liquid distribution data which represent an expected liquid distribution. The expected liquid distribution can be a simulated distribution, for example a distribution as it was simulated for determining the infusion parameters, or it can be a desired or target liquid distribution.

The method also preferably comprises the step of simulating future liquid distribution data, which represent a future liquid distribution, using the actual liquid distribution data. This means that, starting from the actual or present distribution, the future development of the liquid distribution is simulated, for example in an analogous way to the simulation described above. This is particularly useful if the actual liquid distribution differs from the expected liquid distribution and it is to be determined whether or not the infusion will be successful if the infusion parameters are kept the same. The simulation is preferably also based on the verification scan data or the monitoring scan data, which represent the state of the tissue in the body region. If the simulation is based on the verification scan data, then the additional data, transformed using the transformation rule as explained above, can be used to predict the future liquid distribution. If the simulation is based on the monitoring scan data, a new transformation rule is preferably determined by performing image fusion of the planning scan data onto the monitoring scan data, in an analogous way to the image fusion explained above.

The additional data, in particular the DTI data, transformed using the new transformation rule, can then be used to predict the future liquid distribution.

The method optionally also comprises the steps of determining a new source volume of the liquid from the monitoring scan data or the actual liquid distribution data, and determining new infusion parameters from the new source volume and at least one of the verification scan data and the monitoring scan data. The infusion can change the structure of the tissue, in particular in the vicinity of an outlet port of the infusion device, in which case it is advantageous to adapt the source volume to the new tissue structure and re-determine suitable infusion parameters. This is achieved in particular by simulating the liquid distribution as outlined above. This simulation can be based on the verification scan data and/or the monitoring scan data as a representation of the tissue structure. The simulation can also be based on the additional data, in particular the transformed DTI data, once they have been transformed using a corresponding transformation rule as explained in the previous paragraph.

Preferably, the method also optionally comprises the step of determining the time of the next monitoring scan from at least one of the actual liquid distribution data and the future liquid distribution data. Due to the possible risks to the patient of some imaging modalities, a high frequency of monitoring scans is inadvisable. In this optional step, the time of the next monitoring scan is determined. The time interval between two monitoring scans can for example depend on at least one of: the difference between the actual liquid distribution and an expected liquid distribution; the future liquid distribution; or an uncertainty, represented for example by a measure of uncertainty, in the prediction of the future liquid distribution.

In short, the method starts by determining a planned position for an infusion device from planning scan data. The method then determines the infusion parameters from verification scan data acquired after the infusion device has been placed. In an optional step, the actual liquid distribution is determined from monitoring scan data acquired during the infusion. In another optional step, new infusion parameters are determined. It is to be noted that the present method does not comprise any surgical steps; the steps of the present method are merely performed in sequence with one or more surgical steps or in parallel with the infusion and do not encompass any actions performed on the body of a patient.

The method in accordance with the invention is in particular a data processing method. The data processing method is preferably performed using technical means, in particular a computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular any kind of electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The present invention also relates to a program which, when running on a computer or loaded onto a computer, causes the computer to perform the method specified above and/or to a program storage medium on which the program is stored and/or to a signal wave, in particular a digital signal wave, carrying information which represents the program.

Within the framework of the invention, computer program elements can be embodied by hardware and/or software (this includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of the present invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention also relates to a computer comprising a calculating unit on which the program specified above is running or into the memory of which said program is loaded.

It is within the scope of the present invention to combine one or more features of the explained embodiments or options to form a new embodiment as long as this is technically sensible and feasible.

The present invention shall be explained in more detail in accordance with a preferred embodiment by referring to the accompanying drawings, which show.

Figure 1A:
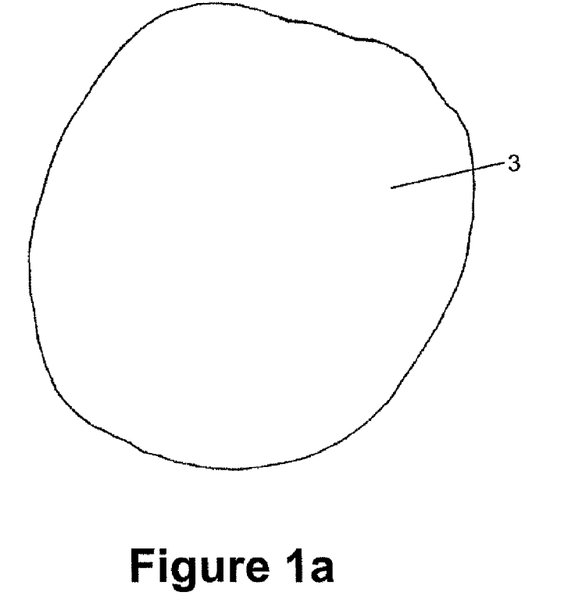
FIG. 1 an infusion situation before and after an infusion device is positioned.

FIG. 1a shows the outline of a tumour 3 as it appears in a three-dimensional medical image. The medical image is represented by planning scan data. The outline of the tumour 3 is for example determined using segmentation, as is known in the prior art. The tumour 3 is surrounded by healthy tissue, for example healthy brain tissue.

The present invention relates to planning an infusion in which a medical liquid is infused into the body comprising the tumour 3 in order to treat the tumour 3. In the present embodiment, "planning" relates to the position of an infusion device and to infusion parameters such as the flow rate, the infusion duration and properties of the medical liquid such as its viscosity or the amount of an active substance within the liquid.

In this document, the "position" of the infusion device 1 relates not only to the position of the outlet 2 of the infusion device 1 but also to the path or trajectory described by the infusion device 1 within the tissue. This path can have an influence on the backflow length. If the backflow along the infusion device 1 ends in a cavity, such as a sulcus of the brain, then the medical liquid will propagate into the cavity rather than into the target tissue such as the tumour 3.

Figure 1B:
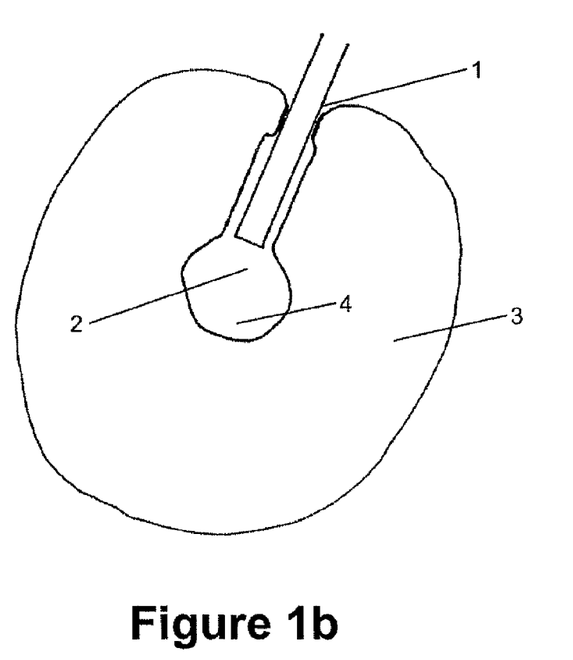

FIG. 1b shows an infusion situation as it may be depicted in three-dimensional image data which are represented by verification scan data. In this situation, a part of an infusion device 1 penetrates into the tumour 3. The infusion device 1 is part of an infusion apparatus (not shown) which holds and/or delivers the medical liquid. The infusion device 1 also extends through healthy tissue surrounding the tumour 3. An outlet or port 2, through which the liquid is infused, is provided at one end of the infusion device 1.

Due to various effects, the medical liquid does not propagate into the tumour 3 directly at the outlet 2. Instead, a source volume 4 is formed, from which the medical liquid propagates into the tumour 3. This source volume 4 typically consists of several parts. One such part is a backflow volume surrounding a part of the infusion device 1, starting at its distal end comprising the opening 2. The backflow volume is formed by the medical liquid flowing along the infusion device 1 rather than into the tumour 3, because the flow resistance along the infusion device 1 is lower than the flow resistance into the tumour 3. Another part of the source volume 4 is an air bubble volume which is formed by the introduction of the infusion device 1 and/or by air which was contained in the lumen of the infusion device 1 and pushed out of the port 2 by the medical liquid.

Figure 2:
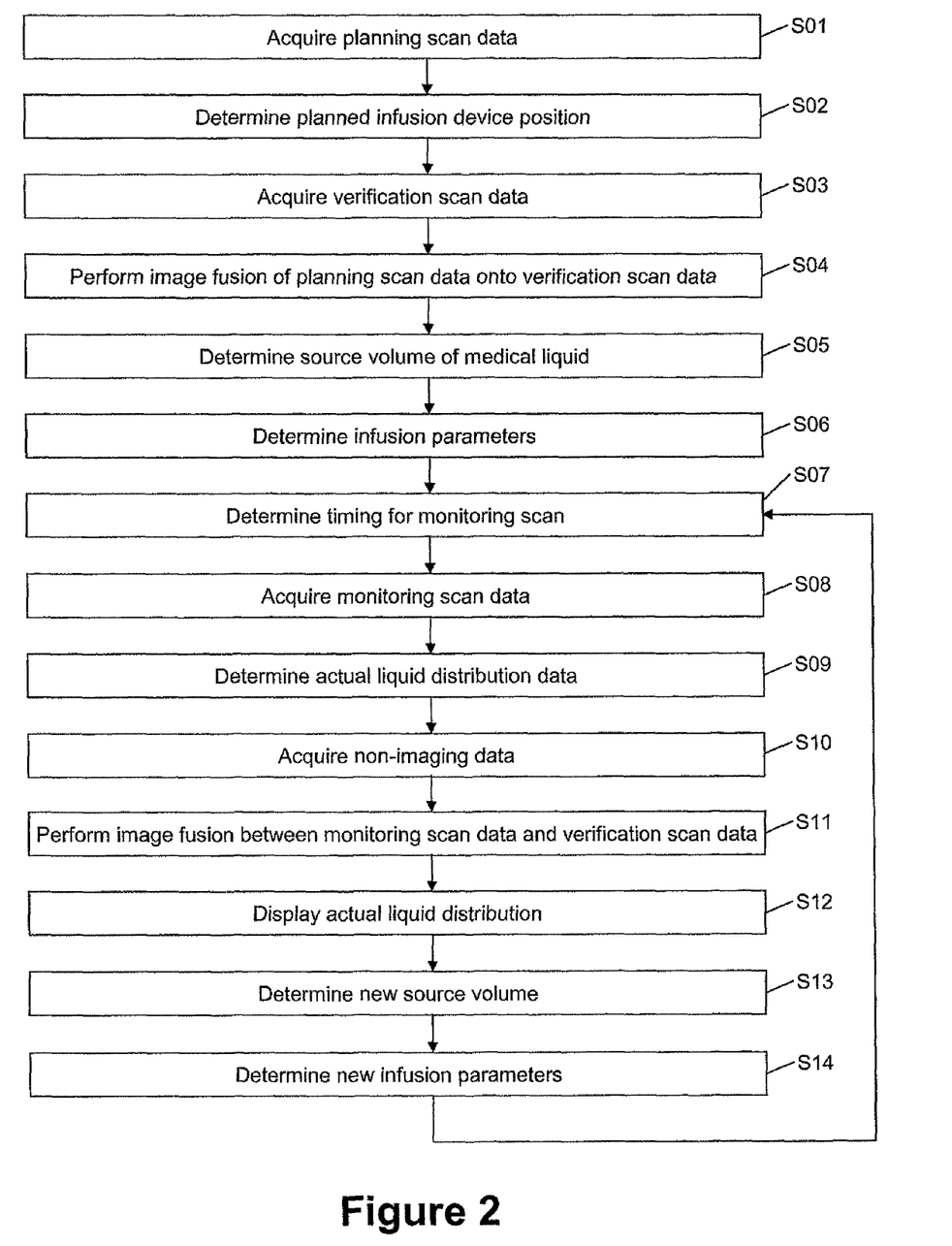
FIG. 2 a flow diagram of the method according to the present invention.

FIG. 2 shows a flow diagram of a method for planning an infusion. In step S01 of the method, planning scan data are acquired. The planning scan data represent a medical image of at least a body region of a patient, wherein the medical image is obtained by a planning scan before the infusion device 1 is positioned. The body region comprises at least some and preferably all of the tumour 3. The medical image can be obtained by any suitable modality, such as MRT, MRI, CT, X-ray or ultrasound. Preferably, DTI (diffusion tensor imaging) data are derived from the planning scan data. DTI data represent a discrete diffusion direction or a probability distribution of diffusion directions for each element, such as a pixel or voxel, of the medical image. The DTI data therefore indicate the direction in which a molecule at a particular position will propagate. Segmentation data are also preferably derived from the planning scan data. The segmentation data assign each pixel or voxel of the medical image to a particular structure.

In step S02, a planned infusion device position is determined. This planned position of the infusion device 1 is a position which is suitable for performing an infusion which would have a desired effect and in particular lead to a desired liquid distribution in the tumour 3.

Figure 3:
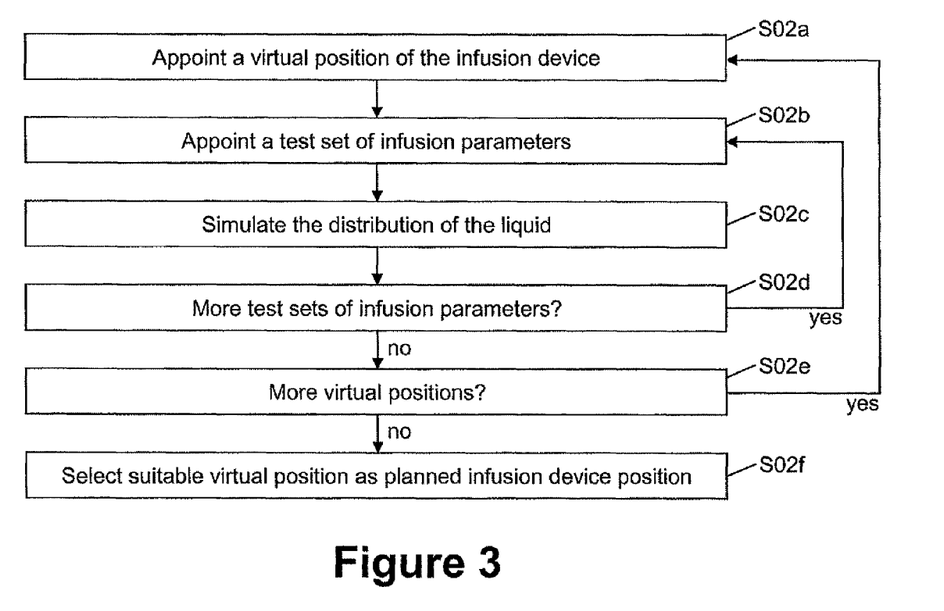
FIG. 3 step S02 of FIG. 2 in more detail.

A detailed embodiment of step S02 is shown as a flow diagram in FIG. 3. This embodiment is based on a stochastical simulation of the liquid distribution. In step S02a, a virtual position of the infusion device is appointed. In step S02b, a test set of infusion parameters is appointed. "Appointing" an entity means here that a value or a set of values for this entity is assumed, for example selected from a list of possible values or sets of values or determined on the basis of the last appointed value or set of values.

In step S02c, the distribution of the liquid is simulated on the basis of the virtual position of the infusion device and the test set of infusion parameters. The simulation is also based on the planning scan data. The simulation is a stochastical simulation of the distribution of the liquid. This means that a starting distribution is assumed, for example comprising a source volume filled with the liquid. The propagation of the liquid is then predicted, for example on the basis of the DTI data, and applied to the starting distribution of the liquid. This results in a new distribution at a later point in time. The development of the distribution over time is predicted by performing a plurality of iterative simulation steps, with the updated liquid distribution of one step being used as the starting distribution in the next step. The simulation preferably adduces other parameters such as the properties of the liquid and the properties of the infusion device.

The simulation of the distribution of the liquid in step S02c can optionally take into account the source volume which will be formed by the infusion device 1 and the medical liquid. The backflow length along the infusion device 1 can for example be determined from the properties of the infusion device 1 and the surrounding tissue. In addition, the size of an air bubble can be predicted from the amount of air which is held in the lumen of the infusion device 1 and pushed out through the opening 2 by the medical liquid.

If the simulation for the virtual position and the test set of infusion parameters is completed, a check is made in step S02d as to whether or not there are any more test sets of infusion parameters. If this is the case, the method returns to step S02b, in which a new test set of infusion parameters is appointed, and the simulation is repeated using this new test set. If there are no more test sets of infusion parameters, a check is made in step S02e as to whether or not there are any more virtual positions. If this is the case, the method returns to step S02a, in which a new virtual position of the infusion device is appointed, and the process continues using this virtual position. If there are no more virtual positions, a suitable virtual position is selected in step S02f as the planned infusion device position.

In the inner loop of steps S02b to S02d, a plurality of test sets of infusion parameters are assumed for simulating the distribution of the liquid. For each virtual position, the test set of infusion parameters which results in the best distribution of the liquid is found and preferably stored. The definition of the best distribution can depend on the infusion to be planned. One aim can for example be to obtain a particular liquid concentration in a target tissue, such as the tumour 3, while obtaining the lowest possible liquid concentration in the surrounding (healthy) tissue. Another aim could be to achieve a desired liquid concentration in the target tissue in the shortest possible time.

Once the suitable virtual position has been selected in step S02f, the test set of infusion parameters which leads to the best distribution of liquid for this virtual position is preferably stored for later use.

In general, another loop can be placed around the loop in which virtual positions are assigned. In this additional outer loop, one or more types of infusion device are appointed, such as for example infusion devices which exhibit different rigidities, materials and/or inner or outer diameters. The type of infusion device which results in the best liquid distribution can be determined in this additional loop.

In step S03, verification scan data are acquired. The verification scan data represent a medical image of the body region of the patient after the infusion device 1 has been positioned. It is to be noted that the actual positioning of the infusion device 1 occurs at an intermediate stage between steps S02 and S03 and is not itself part of the present invention.

The actual position of the infusion device 1 can be determined from the verification scan data. This position can differ from the planned position, for example due to imprecise positioning or a movement of the target tissue, such as a shift of the brain within the skull. It is also possible to determine the position and size of air bubbles within the target tissue from the verification scan data. The verification scan can be performed using any modality which can be used for the planning scan. However, it is preferred if the same modality is used for the planning scan and the verification scan.

A significant period of time may elapse between the planning scan and the verification scan, in particular if the planning scan is rather complex, as is for example the case when obtaining DTI data. In order to compensate for this, image fusion of the planning scan data onto the verification scan data is performed in step S04, wherein a transformation rule is obtained which transforms the medical image, represented by the planning scan data, so as to match the medical image in the verification scan data. Several conditions can be used for this matching process such as are known in the prior art. The image fusion can be a rigid or elastic fusion. Using the transformation rule obtained in step S04, the additional data, such as DTI data and/or segmentation data, can be transformed so as to correspond to the medical image represented by the verification scan data.

In step S05, the source volume of the medical liquid is determined. Air bubbles which are part of the source volume can for example be identified in the verification scan data. The backflow volume along the infusion device 1 can be predicted on the basis of at least one of: the properties of the infusion device 1; the properties of the medical liquid; and the infusion parameters.

In step S06, the infusion parameters are determined. This determination process is shown in more detail in the flow diagram of FIG. 4.

Figure 4:
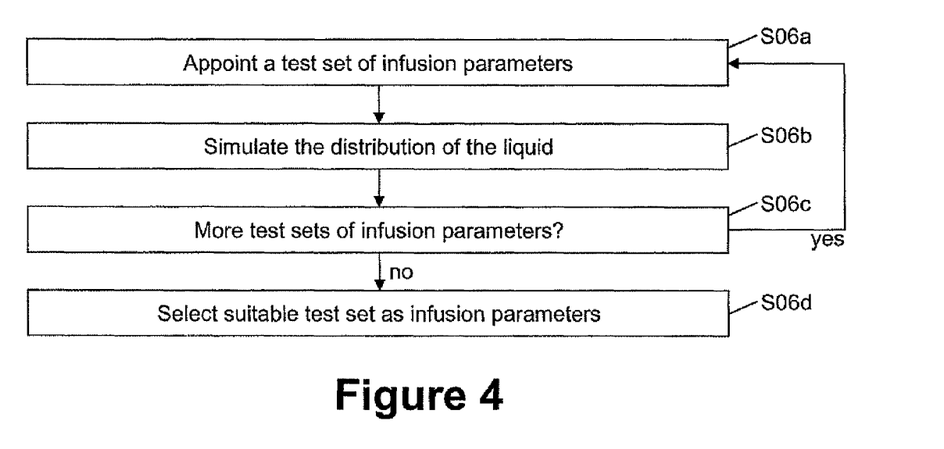
FIG. 4 step S06 of FIG. 2 in more detail.

In step S06a, a test set of infusion parameters is appointed and used in the simulation of the distribution of the liquid in step S06b. This simulation can be performed in an analogous way to the simulation in step S02c, such that a repetition of the detailed description is omitted here.

In step S06c, a check is made as to whether or not there are any more test sets of infusion parameters. If this is the case, the process returns to step S06a in order to appoint a new test set of infusion parameters and subsequently simulate the distribution of the liquid in step S06b using this new test set. If there are no more test sets of infusion parameters, a suitable test set is selected as the infusion parameters in step S06d. The criteria for selecting a test set can be the same as in step S02f explained above. Within step S06, the source volume can be adapted in accordance with the appointed test set of infusion parameters. This provides for the fact that parameters such as the flow rate or the pressure of the medical liquid influence the backflow length.

The determined infusion parameters are then provided to the infusion apparatus in order to control the administration of the medical liquid. The method can end at this point. Alternatively, the infusion can be monitored by performing steps S07 to S14 as explained below.

In step S07, the timing for a monitoring scan is determined. The time of the first monitoring scan can be a fixed time after the start of the infusion. Alternatively, the time of the monitoring scan is calculated on the basis of the simulated distribution of the medical liquid and/or the uncertainty associated with the simulated distribution due to the stochastical nature of the simulation.

In step S08, monitoring scan data are acquired. The monitoring scan data represent a medical image of the body region of the patient during the infusion and are obtained by performing a monitoring scan.

In step S09, actual liquid distribution data are determined. The actual liquid distribution data are in particular derived from the monitoring scan data. The actual liquid distribution data can be determined by using a contrast agent which is co-infused with the medical liquid or is part of the medical liquid.

In step S10, non-imaging data are acquired. This non-imaging information can include in-line pressure profiles or in-line fluid flow profiles within the infusion device 1. These non-imaging data can be compared to reference data determined from the infusion parameters.

In step S11, image fusion is performed between the monitoring scan data and the verification scan data, such that the medical images represented by these data match.

In step S12, the actual liquid distribution is displayed. In this step, the actual course of the infusion can be visualised, for example to an operator.

The actual liquid distribution can be compared to a desired liquid distribution, for example the distribution predicted by the simulation. If the distributions do not match, i.e. are not for example within a tolerable deviation, then suitable measures can be taken.

One possible measure is to simulate the future liquid distribution on the basis of the actual liquid distribution and the non-imaging data. It is then possible to decide whether or not continuing the infusion using the present parameters would lead to a desired liquid distribution. If this is not the case, or as an alternative measure, the infusion parameters can be adapted. For the purpose of this approach, a new source volume is determined in step S13, in an analogous way to step S05 but on the basis of the monitoring scan data instead of the verification scan data.

The new infusion parameters are then determined in step S14, in an analogous way to the infusion parameters determined in step S06 but on the basis of the new source volume determined in step S13. The simulation is preferably based on the monitoring scan data and alternatively on the verification scan data.

The new infusion parameters can then be provided to the infusion apparatus. The method can end at this point or can return to step S07 to start a new monitoring loop.

Several modifications to the workflow shown in FIG. 2 are possible. Step S12 (displaying the actual liquid distribution) can for example be omitted. Step S13 (determining the new source volume) can also be omitted, in which case the source volume determined in step S05 is preferably used in step S14. Step S10 (determining non-imaging data) can also be omitted.

Figure 5:
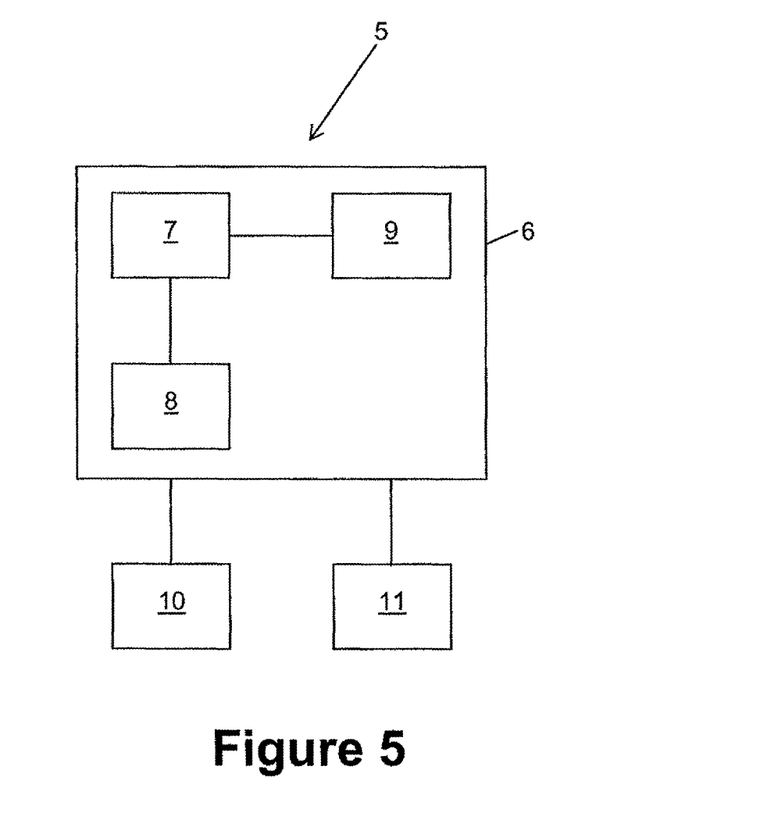
FIG. 5 an apparatus for carrying out the method of the present invention.

FIG. 5 schematically shows an apparatus 5 for carrying out the invention. The apparatus 5 comprises a computer 6. The computer 6 comprises a calculating unit 7, a storage medium 8 and an interface 9. A program which is running on the calculating unit 7 performs the steps of the present method or issues commands for these steps to be performed. A variety of data can be stored in the storage medium 8, such as the planning scan data, the verification scan data, the monitoring scan data, the actual liquid distribution data, the non-imaging data and the transformation rules obtained by image fusion. The computer 6 can receive data, such as those listed immediately above, via the interface 9. The computer 6 can be connected to an imaging apparatus, a network and/or an external storage medium via the interface 9.

The computer 6 is connected to a display device 10 and an input device 11. The display device 10, such as for example a monitor, can be used to display data, such as for example the actual liquid distribution data. The input device 11, such as for example a mouse, a joystick, a trackball or a keyboard, can be used to input commands into the computer 6.

An adaptor can be used to assemble multiple parts of the apparatus or to attach the apparatus to another device. Such an adaptor is also part of the present invention. An adaptor for fixing a (medical) apparatus to one or two support structures is characterised in that the adaptor is constructed in three parts from a bearing part and two support parts, wherein the bearing part can be connected to the medical apparatus, the first support part can be connected to a first support structure, and the second support part can be connected to a second support structure, and wherein the adaptor can assume at least three states: a first state, in which the bearing part is connected, free of clearance, to the first support part only; a second state, in which the bearing part is connected, free of clearance, to the second support part only; and a third state, in which the bearing part is connected, free of clearance, to the first support part and the second support part.

The invention claimed is:

1. A method for planning an infusion of a medical liquid by an infusion apparatus comprising an infusion device, wherein the method is performed by a computer of the infusion apparatus and comprises:
    acquiring, by the computer, planning scan data which represent a medical image of at least a body region of a patient and are obtained by a planning scan before the infusion device is positioned;
    storing the planning scan data in a storage medium of the computer;
    determining, by a calculating unit of the computer, a planned device position from the planning scan data;
    acquiring, by the computer, verification scan data which represent a medical image of the region of the patient after the infusion device has been positioned;
    storing the verification scan data in the storage medium of the computer;
    performing, by the calculating unit of the computer, image fusion of the planning scan data onto the verification scan data in order to obtain a transformation rule for data determined on the basis of the planning scan;
    determining, by the calculating unit of the computer, a source volume of the liquid from the verification scan data; and
    determining, by the calculating unit of the computer, infusion parameters from the verification scan data and the source volume.

2. The method of claim 1, wherein the source volume depends on at least one of: the type of infusion device; air bubbles in the body region; and the flow rate of the liquid.

3. The method of claim 1, wherein the planned position of the infusion device is determined by simulating, by the computer, a distribution of the liquid for several virtual positions of the infusion device on the basis of the planning scan data and automatically selecting, by the compute; as the planned position, the virtual position which best meets the conditions for a liquid distribution described by condition data.

4. The method of claim 3, wherein the liquid distribution for each virtual position of the infusion device is simulated for a plurality of test sets of infusion parameters.

5. The method of claim 3, wherein the simulation of the liquid distribution takes into account the position of the infusion device.

6. The method of claim 3, wherein the infusion parameters are determined by simulating, by the computer, a distribution of the liquid for several test sets of infusion parameters based on the verification scan data and by automatically selecting, by the computer, as the infusion parameters, the test set of infusion parameters which result in a desired liquid distribution, and wherein the test set of infusion parameters used in a first run of the simulation is the test set of infusion parameters corresponding to the virtual position which was selected as the planned position of the infusion device.

7. The method of claim 1, wherein the infusion parameters are determined by simulating, by the computer, a distribution of the liquid for several test sets of infusion parameters based on the verification scan data and by automatically selecting, by the computer, as the infusion parameters, the test set of infusion parameters which result in a desired liquid distribution.

8. The method of claim 1, further comprising the steps of:
    acquiring, by the compute; monitoring scan data which represent a medical image of the region of the patient during the infusion by performing a monitoring scan; and
    determining, by the computer, actual liquid distribution data, which represent the actual distribution of the liquid in the body region, from the monitoring scan data.

9. The method of claim 8, further comprising the step of comparing, by the computer, the actual liquid distribution with an expected liquid distribution.

10. The method of claim 8, further comprising the step of simulating, by the computer, a future liquid distribution using the actual liquid distribution.

11. The method of claim 8, further comprising the steps of:
   determining, by the computer, a new source volume of the liquid from the monitoring scan data or the actual liquid distribution data; and
   determining, by the computer new infusion parameters from the new source volume and at least one of the verification scan data and the monitoring scan data.

12. The method of claim 8, further comprising the step of determining, by the computer, the time of the next monitoring scan from at least one of the actual liquid distribution and the future liquid distribution.

13. A non-transitory computer-readable program storage medium storing a program which, when running on a computer or loaded onto a computer, causes the computer to perform the steps of:
   acquiring planning scan data which represent a medical image of at least a body region of a patient and are obtained by a planning scan before the infusion device is positioned;
   determining a planned device position from the planning scan data;
   acquiring verification scan data which represent a medical image of the region of the patient after the infusion device has been positioned;
   performing image fusion of the planning scan data onto the verification scan data in order to obtain a transformation rule for data determined on the basis of the planning scan;
   determining a source volume of the liquid from the verification scan data and determining infusion parameters from the verification scan data and the source volume.

14. A computer comprising the non-transitory computer-readable program storage medium of claim 13.

* * * * *